United States Patent [19]

Elsheikh et al.

[11] Patent Number: 5,639,924
[45] Date of Patent: Jun. 17, 1997

[54] PROCESS FOR THE PRODUCTION OF 1,1,1-TRIFLUOROETHANE

[75] Inventors: Maher Yousef Elsheikh, Wayne; Michael Sheppard Bolmer, Collegeville, both of Pa.; Jean Pierre Schirmann, Paris, France; John Aloysius Wismer, Washington Crossing, Pa.; Wayne E. Brooks, Paducah, Ky.

[73] Assignee: Elf Atochem North America, Inc., Philadelphia, Pa.

[21] Appl. No.: 346,489

[22] Filed: Nov. 29, 1994

[51] Int. Cl.$^6$ .................................................. C07C 19/08
[52] U.S. Cl. .......................... 570/168; 570/165; 570/166; 570/169
[58] Field of Search ................................ 570/166, 168, 570/165, 169

[56] References Cited

U.S. PATENT DOCUMENTS

| | | | |
|---|---|---|---|
| 2,744,147 | 5/1956 | Milks | 570/168 |
| 2,744,148 | 5/1956 | Ruh et al. | 570/168 |
| 3,231,519 | 1/1966 | Clark et al. | |
| 3,287,424 | 11/1966 | Pacini et al. | |
| 3,644,545 | 2/1972 | Buckman | 570/168 |
| 3,803,241 | 4/1974 | Stolkin et al. | |
| 3,833,676 | 9/1974 | Ukaji et al. | |
| 3,836,479 | 9/1974 | Paucksch et al. | |
| 3,904,701 | 9/1975 | Schultz et al. | |
| 3,965,038 | 6/1976 | Schultz et al. | |
| 4,091,043 | 5/1978 | Ohsaka et al. | |
| 4,147,733 | 4/1979 | Fiske et al. | |
| 4,474,895 | 10/1984 | Foullitier | 470/165 |
| 4,937,398 | 6/1990 | Tung et al. | |
| 5,008,474 | 4/1991 | Wairaevens et al. | |
| 5,243,107 | 9/1993 | Scott et al. | 570/168 |

FOREIGN PATENT DOCUMENTS

| | | |
|---|---|---|
| 0234002B1 | 1/1991 | European Pat. Off. . |
| 0421830A1 | 4/1991 | European Pat. Off. . |
| 0486333A1 | 5/1992 | European Pat. Off. . |
| WO9325507 | 12/1993 | WIPO . |

OTHER PUBLICATIONS

Francis H. Walker and Attila E. Pavlath, Dehydrohalogenation of 1,1,1-Trihaloethanes, *J. Org. Chem.* (30), Mar. 4, 1965, pp. 3284-3285.

McBeth et al., *J. Chem. Soc.*, Dalton Trans., 1990, p. 671.

*Primary Examiner*—C. Warren Ivy
*Assistant Examiner*—Lyman H. Smith
*Attorney, Agent, or Firm*—Ratner & Prestia

[57] ABSTRACT

Process for synthesizing 1,1,1-trifluoroethane (143a) in the gaseous phase by reacting 1,1-defluoro-1-chloroethane in gaseous phase in the presence of a Cr catalyst. The process may be run isothermally or adiabatically, without co-feeding air or other oxygen containing gas, in the presence or absence of a Ni, Co, Zn or Mn cocatalyst for the Cr catalyst. The catalyst may be unsupported or supported with a support preferably selected from activated carbon, alumina and fluorided alumina. The formation of olefin byproduct can be kept to less than 10 ppm in accordance with the process of the invention.

30 Claims, 2 Drawing Sheets

FIG. 1

FIG.2

PROCESS FOR THE PRODUCTION OF 1,1,1-TRIFLUOROETHANE

FIELD OF THE INVENTION

The present invention relates to an improved method for producing 143a (1,1,1-trifluoroethane) by continuous gas phase hydrofluorination of 1,1-difluoro-1-chloroethane using heterogeneous catalysis.

BACKGROUND OF THE INVENTION 1,1,1-Trifluoroethane (143a) is a hydrofluorocarbon (HFC) with zero ozone depletion potential (ODP). The product was described earlier in the literature as an undesirable co-product from processes involving hydrofluorination of 1,1-dichloroethylene (VDC, 1130a) or 1,1,1-trichloroethane (140a). While methods are known for synthesizing 143a, there is a need for a simple, convenient, economical, industrial process for the manufacturing of 143a. The present invention provides a new practical process for the production of 143a with very high conversion and very high selectivity (both over 99%) for 143a.

In U.S. Pat. No. 3,231,519, issued Jan. 28, 1966 and assigned to Union Carbide Corporation, a catalyst composed of coprecipitated iron hydroxide and rare earth oxide, such as dysprosium hydroxide, and zirconium oxide was used to hydrofluorinate 140a to a mixture of 143a, 142b and 1130a. Thus, when hydrogen fluoride (177 g, 8.85 moles) and 1,1,1-trichloroethane (541 g, 4.05 moles) were vaporized over 150 milliliters of the catalyst over a three to four hour reaction period at a temperature of 230°–260° C., to give 1,1,1-trifluoroethane (122 g, 1.45 moles); 1-chloro-1,1-difluoroethane (33 grams, 0.328 moles); 1,1-dichloroethylene (157 g, 1.62 moles) and a small amount of 1-chloro-1-fluoroethylene. The latter two products, 1130a and 1131a, are a waste co-product; conversion was 83.9% and selectivity for 143a was 42.67% under these conditions. Catalysts claimed in this patent are a combination of iron oxide, rare earth oxide, and zirconium oxide. The lifetime of the catalyst was not reported.

U.S. Pat. No. 3,287,424, issued Nov. 22, 1986 and assigned to Stauffer Chemical Company, discloses the hydrofluorination of 1,1,1-trichloroethane (140a) to 1,1,1-trifluoroethane (143a) in a batch process, using arsenic trifluoride as a fluorinating agent and antimony pentafluoride as a catalyst. In Example 3, a mixture of arsenic trifluoride (333.25 grams, 2.53 moles) and antimony pentafluoride (29.9 grams, 0.14 moles) was reacted with methylchloroform (133 g, 1 mole) at 45°–50° C. to produce 1,1,1-trifluoroethane (63 g, 0.75 moles). The fluorinating agent, $AsF_3$, is a highly toxic material and is an expensive reagent for industrial applications.

U.S. Pat. No. 3,803,241, assigned to Dynamit Nobel AG, uses a catalyst composed of chromium (III) chloride supported on alumina, prepared by soaking aluminum oxide pellets in $CrCl_3.6H_2O$ solution (31 wt. %). The catalyst was dried at 200° C. using nitrogen or air, followed by HF activation at 250° C. for 2 hours. In Example 1, following the HF activation, a gaseous stream of 1,1-dichloroethylene and hydrogen fluoride in a molar ratio of 1:3.5 at 150° C. was passed over the catalyst bed at 150° C., to yield 98.8 volume % of 1,1,1-trifluoroethane, 0.2 volume % of 142b, 0.2 volume % of 141b and 0.8 volume % of 1,1-dichloroethylene. After running for quite some time (exact running time not reported), the catalyst was regenerated by heating for 10–15 days. No experimental details were provided on how the catalyst was reactivated nor was there evidence that the catalyst performance improved after the treatment. Although the selectivity and conversion were very high, the catalyst required a very long time for regeneration, which is not practical for industrial applications.

In U.S. Pat. No. 3,833,676, it is disclosed that hydrofluorination of methyl chloroform in a liquid phase batch process can produce very low levels of 1,1,1-trifluoroethane (Example 2). In this example, methyl chloroform (3.73 grams) and hydrogen fluoride (17 g) (molar ratio of HF:methyl chloroform=30.3:1) were mixed together in a stainless steel reactor at 110° C. for 2 hours to produce 2.3 mole % of 141b, 95.5 mole % of 142b and 2.1 mole % of 143a. This process is a liquid phase process and requires very long contact time, which means that it is much less productive compared to continuous gas phase processes.

In U.S. Pat. No. 3,836,479, Example 1, a catalyst composed of boric acid (0.18 kg) mixed with pseudoboehmite alumina (1.2 kg) was prepared and activated using hydrogen fluoride at 350° C. using 2 mole/hr HF and 1 mole/hr nitrogen. After the catalyst was activated, a mixture of HF (0.75 mole/hr) and vinylidene fluoride (feed rate not reported) was passed over the catalyst at room temperature to produce 100% conversion to 143a. (Example 12) The feed stock of this process, 1,1-difluoroethylene, is an expensive compound for industrial application, and it is expected that 143a produced using this process will be expensive.

A bismuth containing catalyst supported on alumina was prepared in Example 1 of U.S. Pat. No. 3,904,701 by soaking alpha-alumina (650 g) in a mannitol solution of $Bi(NO_3)_3.5H_2O$ (153 g). The catalyst was dried at 80° C. for one hour. Subsequently it was activated at 250° C. using a mixture of HF and air. Then a gaseous mixture of 1 part dichloroethylene and 3.2 parts of HF (Example 1) was passed over the catalyst bed at 180° C., with 18 seconds contact time. Analysis of the product obtained indicated that conversion was 99.9%; selectivity for 143a was 99.8% and for 142b it was 0.2%. In all the examples reported in this patent, halogenated alkenes were used as the feed stock. E.g., in Examples 1, 3, 4 and 5; 1,1-dichloroalkene was used as the starting material; in Example 2, vinyl fluoride monomer was used as the organic substrate. The composition of the catalyst of this patent ($Bi/Al_2O_3$) is totally different from that of the catalyst of the present invention. This patent also discloses an improved regeneration process for the above catalyst, by heating the deactivated catalyst in air at a temperature of about 350°–450° C. This regeneration process is claimed in related U.S. Pat. No. 3,965,038.

A continuous liquid phase process for the hydrofluorination of methylchloroform to the mixture of products 141b, 142b and 143a is disclosed in U.S. Pat. No. 4,091,043. The process requires continuous feed of antimony pentachloride in the presence of organic solvent. This will require additional separation equipment to separate the antimony catalyst and the organic solvent, which is troublesome on the industrial scale. The best result for $CH_3CF_3$ selectivity (82.6%) was obtained when the reactor was initially charged with $SbCl_5$ (52.2 mole %) and 0.76 moles of the solvent 1,1,2-trifluoro-1,2,2-trichloroethane. The feed rate of methylchloroform was 0.76 mole/hour; for HF it was 2.32 mole/hour. At 28° C., conversion was 93%, while selectivity for 143a was 82.6%. Selectivity was 17.1% for 142b and 0.3% for 141b. A similar process was described in Atochem S.A.'s European Patent Publication No. 0 421 830 A1, which uses a combination of $SbF_5$ and chlorine gas as a catalyst for a HF/methylchloroform process. The percent selectivity of 143a varied between 1% to 10.3%, depending on the processing conditions. Again, this process requires recovery of the antimony catalyst. In the absence of chlorine gas, the active catalytic species, Sb(V), was reduced to the inactive catalyst species, Sb(III).

In U.S. Pat. No. 4,147,733, Example 2, a catalyst composed of alumina coated with 12 percent by weight of $Cr_2O_3$ and 6% of NiO, was used to hydrofluorinate chlorinated aliphatic hydrocarbons to the corresponding fluoride using aqueous HF, e.g. at 420° C. Feeding a mixture of 38% aqueous HF and 1,1-dichloroethylene vapors at a 3:1 molar ratio of HF/VDC, gave a total conversion of 16.3% to fluorinated product. The selectivity for 143a was 54.1 mole %, while it was 21% for 1-chloro-1-fluoroethylene and 20.4% for vinylidene fluoride. This process requires the use of aqueous HF as a feed stock, which is known to be very corrosive compared to anhydrous HF gas. Furthermore, the presence of the fluoro-olefin as impurity in 143a is undesirable for either refrigerant applications or foam blowing agent applications.

1,1,1-Trifluoroethane was also reported as a major co-product, during the fluorination of vinylidene fluoride, using activated carbon, in U.S. Pat. No. 4,937,398. The process was directed towards the preparation of 1,1,1,2-tetrafluoroethane. Instead, 143a was the major product. The latter product was suggested to be obtained from a process involving HF addition to vinylidene fluoride. HF was disclosed to be generated by hydrolysis of fluorine gas by the moisture on the surface of activated carbon, e.g., when $VF_2$ (8 cc/m) mixed with nitrogen (50 cc/m) was slowly fed over activated carbon (40 grams, saturated with 6 wt % of fluorine gas). At 50° C., conversion was 100% and selectivity for 143a was 82%. Selectivity for 1,1,1,2-tetrafluoroethane (134a) was 18%. The implementation of this process for the production of 143a can be a very difficult task, because fluorine gas addition to olefin is a highly exothermic process.

In U.S. Pat. No. 5,008,474, Example 1, hydrofluorination of 1,1-dichloroethylene in the presence of tin tetrachloride as a catalyst, in a batch liquid phase process, produced 143a in small quantities. E.g., when 5.16 moles of 1,1-dichloroethylene, 16.05 moles of HF and 0.25 moles of $SnCl_4$, were mixed together under continuous stirring, analysis of the product formed showed the following composition: 143a (2.1 mole %), 142b (26.7%), 141b (64.8%), vinylidene chloride (4.1%), 1,1,1-trichloroethane (0.8%) and oligomeric material (1.4%). In Examples 2–4, the yields of 143a were even lower. Thus, the yield of 143a from this process is not high enough for it to be utilized as an industrial process.

European Patent Publication 0 486 333 A1 (134a) discloses the manufacture of 1,1,1,2-tetrafluoroethane by the vapor phase hydrofluorination of 1-chloro-2,2,2-trifluoroethane (133a) in the presence of a mixed catalyst composed of oxides, halides and/or oxyhalides of chromium and nickel on a support of aluminum fluoride or a mixture of aluminum fluoride and alumina. In (comparative) Example 3, it is taught that the presence of nickel, together with chromium, in the catalyst, enhances both the activity and stability of the catalyst.

International Patent Publication W093/25507 is directed, more broadly, to the vapor phase hydrofluorination of a halocarbon (having at least one halogen other than fluorine) with anhydrous HF, at a temperature above 200° C., in the presence of a catalyst comprising a chromium compound and at least one transition metal compound selected from the oxides, halides and oxyhalides of nickel, palladium and platinum. The catalyst may be unsupported, supported or mixed with an appropriate bonder. Suitable supports are taught to include aluminum oxide, aluminum fluoride, aluminum oxyfluoride, aluminum hydroxyfluoride and carbon. This publication also teaches the importance of the presence of nickel in the catalyst, together with chromium, in order to obtain high rates of conversion and prolonged catalyst activity. 1,1-difluoro-1-chloroethane (142b), the starting material of the process of the present invention, while within the generic disclosure of this publication, is not expressly mentioned therein.

The prior art also describes processes that produce 143a which are based on hydrofluorinating either 140a or 1130a. The first compound (140a) is expected to be regulated by the U.S. federal government in the near future. The second compound (1130a) is known to undergo cationic polymerization to produce low molecular weight polymer and thereby deactivate the catalyst. (See McBeth et al., J. Chem. Soc., Dalton Trans., (1990) 671.) In many cases, it is believed that, if an inhibitor is added to the feed stream, it is likely to poison the catalyst. There is need for a simple, convenient and economical process for the production of 143a that avoids the foregoing problems.

SUMMARY OF THE INVENTION

This invention provides a novel process for manufacturing 143a in an economical, industrially feasible manner, which is based on continuous gas phase hydrofluorination using heterogeneous catalysis. The organic feed is 1,1-difluoro-1-chloroethane (142b) and the fluorinating agent is HF. More particularly, we have discovered that 143a can be produced very efficiently, with conversion rates and selectively each in excess of 99%, while avoiding the formation of olefinic byproducts, by vapor phase fluorination of 142b at a molar ratio of HF:142b in excess of 1:1, and preferably in excess of 2.5:1 in the presence of a Cr catalyst, which may be unsupported or supported, in the absence or presence of a cocatalyst selected from nickel, cobalt and manganese salts. That these exceptional high yields and selectivity for 143a could have been achieved by the hydrofluorination of 142b, particularly when using a chromium catalyst, even when unsupported and without a cocatalyst, was not predictable from the references discussed above. In the absence of catalyst, treating 142b with HF at 140° C., using a molar ratio of HF/142b of 3 and 47 seconds of contact time, gave zero % conversion. In the presence of catalyst, conversion was very high. While the catalyst can be any (supported or unsupported) chromium salt, the two catalysts that we have used to provide high conversion rates in this process are $CrF_3.4H_2O$ (powder or pelletized), and $Cr/Ni/AlF_3$. Using these catalysts, conversion was very high (over 99%) and selectivity for 143a was also very high (over 99%).

These catalysts were subjected to severe testing, such as high temperature (100°–325° C.), the presence of a high concentration of HCl (32% in the total feed stream) as well as 141b and 1,1,1,3,3-pentafluorobutane (365). Change in % conversion was minimum and selectivity for 143a was still >99.9%. These results are unexpected because it is known that 142b can be dehydrohalogenated to 1,1-difluoroethylene (1132a) and 1-chloro-1-fluoroethylene (1131a). E.g., when 142b was passed over an $AlF_3/Al_2O_3$ bed at 300° C., conversion for 1132a was 10.4% and 79.5% for 1131a. (Walker and Paylath, "Dehydrohalogenation of 1,1,1-Trihaloethanes," J. Org. Chem. (30), 1965 (3284).) On the other hand, 143a can be dehydrofluorinated to 1132a at 500° C. with a 32% conversion rate. (See European Patent Publication No. 0 234 002 B1.)

In this investigation, under isothermal conditions, provided that the molar ratio of HF:142b was greater than 1:1, we have not detected any level of olefinic product at a reaction temperature below 275° C. when the above molar ratio was up to 2.5:1, or at a reaction temperature below 325° C. when that molar ratio was greater than 2.5:1.

Also, whereas the process of WO93/25507 requires a reaction temperature of greater than 200° C., in the process of the present invention, excellent yield and selectivity are obtained at reaction temperatures as low as 100° C.

In another embodiment, the process may be run under adiabatic conditions, e.g. in a continuous, plug flow adiabatic reactor.

BRIEF DESCRIPTION OF THE FIGURERS

DETAILED DESCRIPTION OF THE INVENTION

Figure 1:
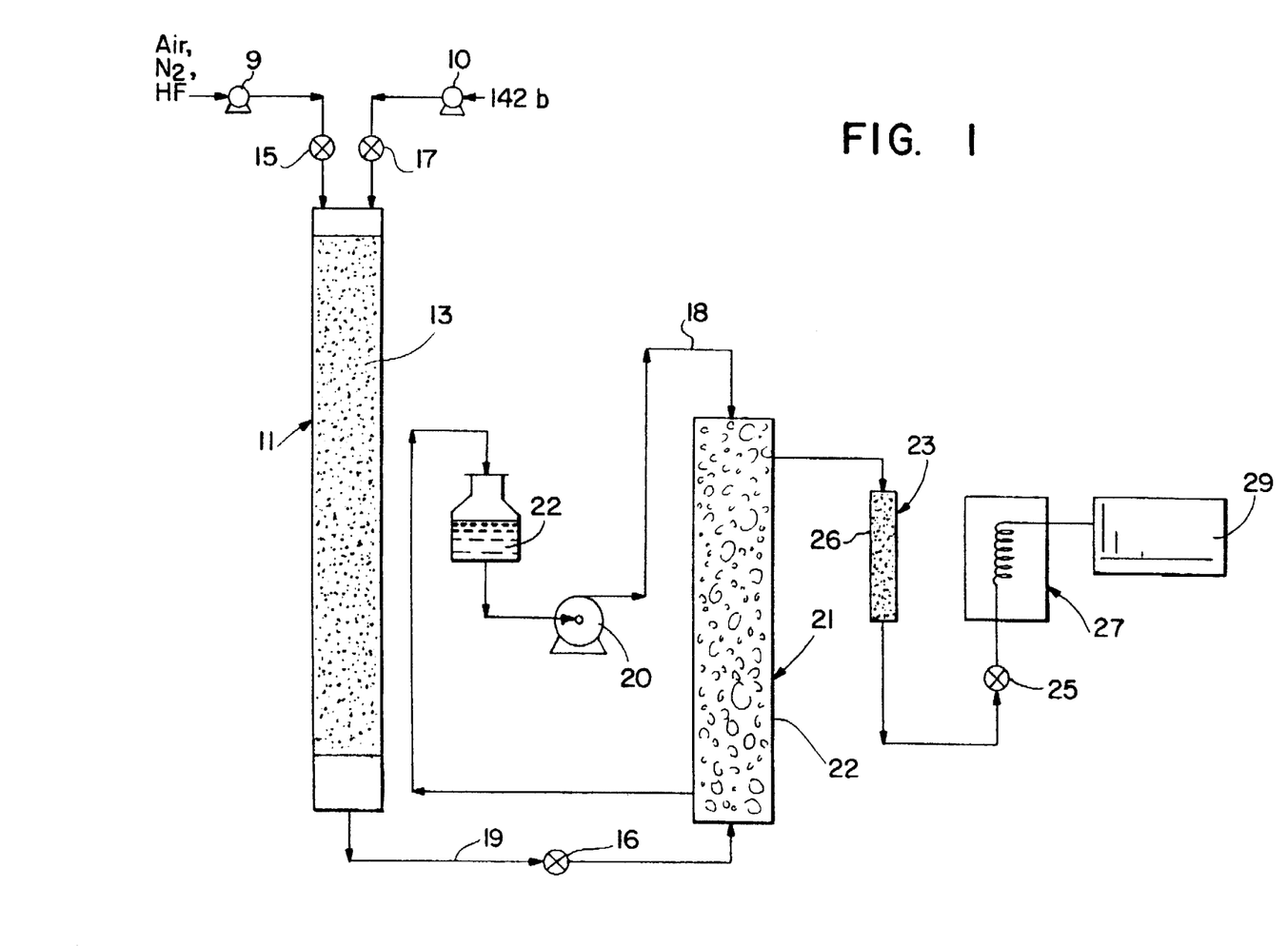
FIG. 1 is a schematic diagram of a reactor suitable for carrying out the process of the invention.

FIG. 1 illustrates a presently preferred reactor for carrying out the process of the present invention for preparing 143a by hydrofluorinating 142b. This reactor will be described in greater detail below in connection with Example 1.

In the process of this invention, 142b and HF are passed through the catalyst bed in a reactor at the specified conditions for reacting, and then the 143a product is purified. Byproduct HCl and unreacted HF may be removed by any number of methods known to the art, such as absorption in water or caustic solution or on solid absorbants, distillation, or membrane separation. Any unreacted 142b or byproduct 141b or olefins (1,1-difluoroethylene, 1,1-chlorofluoroethylene, 1,1-dichloroethylene) can also be removed, e.g., by distillation, absorption in either liquids or solids, or membrane separation.

Any olefins produced in the first reactor can be reacted with HF in a second reactor operating at a lower temperature than the first reactor (Example 19). The thermodynamic equilibrium between olefins and saturated compounds strongly favors saturated compounds at lower temperatures. This configuration makes it possible to use a lower HF:142b molar ratio, such that olefins are produced in the first reactor and converted in the second reactor. This would minimize the amount of unreacted HF that would have to be neutralized or recycled. Unreacted HF can be separated and recycled to the first reactor.

Figure 2:
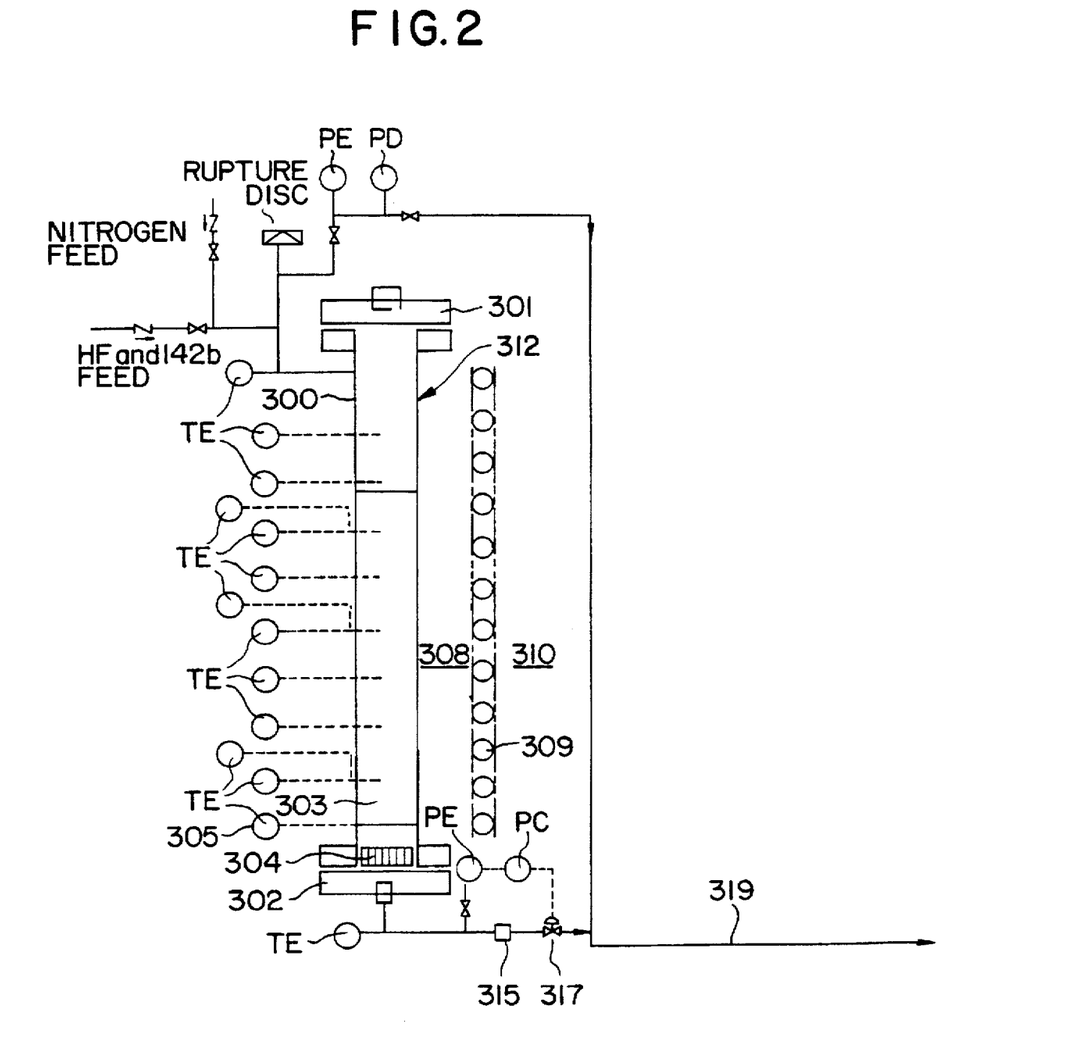
FIG. 2 is a schematic diagram of a pilot version of an adiabatic reactor used for conducting the experiments of Examples 21–26.

FIG. 2 illustrates a pilot adiabatic reactor suitable for carrying out the process adiabatically, as in Examples 21–26 below. This reactor will be described in greater detail below in connection with those examples.

The feed source can be pure 142b and HF or other streams containing these two compounds. 142b can be made by the reaction of HF with either 140a or 1130a. The product of this reaction will usually contain unreacted HF and HCl, as well as 141b byproducts. The use of unpurified feed streams containing 141b and HCl is illustrated in Examples 2, 3, 4, 5, 6, 10, and 11 below.

The reactor can be any vessel that allows the contact of the reactants with the catalyst for sufficient time to achieve the desired conversion. Materials of construction should be able to withstand HF and HCl at reaction temperatures, which are known to those skilled in the art. A plug flow reactor is preferred over a mixed reactor, such as a fluidized bed, in order to achieve high conversion in an efficient manner. The reactor can be cooled or not cooled, as long as the proper reaction conditions are maintained.

The catalyst can be any chromium salt, supported or unsupported. In addition, salts of other metals, such as nickel, cobalt, manganese and zinc can be used as supported or unsupported co-catalysts. Presently preferred supports are $Al_2O_3$ and fluorided $Al_2O_3$. Other supports that may be used include activated carbon as well as other catalyst supports known in the art. We presently prefer to use unsupported $CrF_3 \cdot 4H_2O$ or supported $Cr/Ni/AlF_3$, as indicated in the following examples.

As noted above, the process can be carried out using 142b as a feed and 1,1-dichloro-1-fluoroethane (141b), 1,1,1,3,3-pentafluorobutane (365) or HCl as a co-feed. The process can be carried out at a temperature between 30° C. and 400° C., preferably between 30° and 280° C., more preferably between 100° and 250° C., more preferably between 120° C. and 200° C. In another preferred embodiment, the reaction temperature is between 280° and 350° C. Contact time can be varied from 1–100 seconds and is preferably between 5 and 15 seconds. The catalyst has to be activated first using nitrogen, air or HF/142b at a temperature between 100° C. and 650° C., preferably between 200° C. and 500° C. Hydrofluorination can be performed at a pressure between 1 atmosphere (0 psig) and 200 psig, preferably between 1 atmosphere and 150 psig. The molar ratio of HF:142b can vary between greater than 1:1 and 20:1, preferably between greater than 1:1 and 10:1. More preferably, it is between 2:1 and 5:1.

An important aspect of the invention is the ratio of HF to R142b in the feed. Ideally, this would be very close to 1 to 1 to minimize the need for downstream separation. However, at low HF ratios, non-selectives (unwanted by-products) are formed. In particular, three different unwanted olefins can form: vinylidene fluoride (1132a), vinylidene chlorofluoride (1131a), and vinylidene chloride (1130a). These are decomposition products of 142b. These unsaturated compounds are undesirable in the final product even in small quantities. Therefore, they must be either destroyed or removed from the reaction product by a separation method after the reaction is completed and the product is removed from the reactor. These olefins are believed to be precursors to coke formation, which is the major cause of catalyst deactivation. Thus, in order to avoid olefin formation, we have found that the HF/142b molar ratio should be greater than 1:1. There is no upper limit on the HF/142b ratio, although ratios above 10:1 would be economically impractical, both with respect to reactor productivity and separation requirements.

The HF/142b ratio needed to avoid olefin formation is also affected by the reaction temperature. In general, higher ratios are required at higher reaction temperatures in order to avoid olefin formation. We have found that ratios of HF/142b of greater than 1:1 are suitable for reaction temperatures up to 280° C. At reaction temperatures above 280° C., we prefer to use a minimum HF/142b ratio of 2.5:1.

The reactor effluent will contain 143a, HCl, and HF. In the process of the invention, conversion is generally in excess of 99.5%, so that there is very little 142b in the effluent. The acids can be either scrubbed out by caustic washing or recovered by distillation. If distillation is used, a pressure distillation is needed to recover HCl with conventional refrigeration. The boiling point of HCl at 130 psig is −26° F. Therefore, if the reactor effluent is to feed the distillation train directly, it is advantageous to run the reactor under pressure. Following HCl distillation, the 143a can be distilled overhead while HF is recovered as bottoms. The overhead product from this distillation would be about 10 mol % HF, which is an azeotropic composition with 143a. This material would then be caustic scrubbed to remove the HF and then dried. The effluent from this system should be 143a with a purity level of about 99.9%. If ultrapurification were desired, the unreacted 142b could be recovered as the bottoms fraction of another distillation column and recycled to the reactor. There are alternative distillation sequences to this distillation sequence. The HF could be recovered in the first column with the HF/143a azeotrope and HCl going overhead. HCl could then be recovered by distillation or all of the acid scrubbed. The final 143a recovery step consists of compression and condensation of this volatile material.

The adiabatic process of the invention provides a method whereby 143a can be made at high enough conversion and selectivity to recover it as product using only an acid removal system. It does this with a very simple reactor design (see FIG. 2) and a very specific range of initial temperatures and HF/142b molar feed ratios.

An extrapolation of this technology is to use 141b or mixtures of 141b and 142b as a feedstock. This is possible because the 141b to 142b reaction has a very mild exotherm (about 1 kcal/mol).

I. Fluorination of 142b using $CrF_3.4H_2O$

EXAMPLE 1: Fluorination of 142b.

Chromium fluoride hydrated powder ($CrF_3.4H_2O$, 200 grams), available from Elf Atotech, was mixed with approximately 10 grams of alumina, and the intimate mixture was pelletized using a catalyst pelletizer. The pelletized catalyst 13 (⅛ inch×⅛ inch) (81 grams) was evaluated in a fixed bed ¾ inch (inner diameter) by 12 inch Hastelloy reactor 11, shown in FIG. 1. It was heated gradually to 450° C. in a stream of air (20 cc/m) from valve 15 for 18 hours, followed by HF activation (200 cc/m of HF from valve 15 for 18 hours). The temperature was then lowered to 200° C., and a mixture of HF and 142b (molar ratio 1.47) was fed through valves 15 and 17, respectively, of the reactor with a contact time of 35.6 seconds. The reaction products were removed at the bottom of reactor 11 through line 19 and backpressure regulator 16, and were then passed through a scrubbing tower 21, counter current to a stream 22 of alkaline solution, for example, 1–5 normal aqueous potassium hydroxide, which was circulated through line 18 by pump 20, to remove unreacted HF. Alternatively, the HF can be removed by distillation or other methods known in the art. Other aqueous hydroxides, such as sodium or calcium hydroxide suspension, can also be used as the alkaline solution. The product obtained was then passed through a drying tower 23, packed with a drying agent 26, such as anhydrous calcium sulfate. The conversion was periodically checked by passing product automatically through valve 25 to a gas chromatograph 27 equipped with electronic integrator 29. In the apparatus of FIG. 1, pumps 9 and 10 and a backpressure regulator at 16 facilitate operations of the apparatus at higher pressures, e.g. in excess of 100 psig.

Conversion was 100% and selectivity for 143a was also 100%. The process ran under these conditions for 32 hours. This clearly indicates that $CrF_3$ is a very good catalyst for hydrofluorinating 142b to 143a, without co-feeding air to maintain the catalyst activity. (Table 1, Ex. 1.)

EXAMPLE 2: Fluorination of 142b in the presence of 141b.

Following the completion of Example 1, a mixture of 141b and 142b in equimolar quantities was fed to the reactor of Example 1 together with HF. The molar ratio of HF to the total 141b and 142b (2×141b+142b) was 1.33; contact time was 39.4 seconds; conversion was 100% and selectivity of 143a was also 100%. The process ran continuously for 24 hours at 200° C. (between hours 32 and 56). This shows that $CrF_3$ catalyst can be used to hydrofluorinate, with great efficiency, a blend of 141b and 142b to the desired product, 143a, without forming co-products. (Table 1, Ex. 2.)

EXAMPLE 3: Fluorination of 142b in the presence of 141b and HCl at 200° C.

The feed mixture of HF, 141b and 142b as described in Example 2, together with HCl (38 mole %) formed the total feed to the reactor used in the previous examples. Contact time was 24.4 seconds, conversion was 99.9% and selectivity for 143a was 99.9% (the other 0.1% [nonselective products] actually represents impurities present in the 141b feed). The process ran under these conditions for 66 hours (between hours 56 and 122) without any evidence of catalyst deactivation. This shows that co-feeding a mixture of 141b and 142b together with HCl does not decrease the performance of $CrF_3$ catalyst. (Table 1, Ex. 3.)

EXAMPLE 4: Fluorination of 142b in the presence of 141b and HCl at 250° C.

The same feed conditions reported in Example 3 were used to evaluate the catalyst at 250° C. Contact time was 23.8 seconds, conversion was still very high (99.9%) and selectivity for 143a was also 99.9%. The process ran steadily under these conditions for 28 hours (between hours 122 and 150). These data suggest that $CrF_3$ catalyst is a durable catalyst to hydrofluorinate a mixture of 141b, 142b and HCl at high temperature without forming a major co-product. (Table 1, Ex. 4.)

EXAMPLE 5: Effect of contact time.

Example 4 was repeated except that contact time was lowered to 17.8 seconds by increasing the feed rate of HF, 141b and 142b. Conversion under these conditions was 99.9% and 143a selectivity also was 99.9%. The process ran continuously under these conditions for 74 hours (between hours 150 and 224). (Table 1, Ex. 5a.) When Example 4 was again repeated, this time lowering the contact time to 12.9 seconds, both conversion and selectivity for 143a remained at 99.9%. (Table 1, Ex. 5b.) Upon raising the reaction temperature to 300° C. and further lowering the contact time to 11.7 seconds, the % conversion and selectivity, while somewhat reduced (99.5 and 99.1%, respectively) still exceeded 99%. (Table 1, Ex. 5c.)

EXAMPLE 6: Effect of lower temperature on the catalyst performance.

When the reaction temperature was lowered to 100° C., using the same molar ratio as in Example 2, but a contact time of 44.9 seconds, conversion was only 17% and selectivity was still 100%. The process ran under these conditions for 63 hours. (Table 1, Ex. 6a.) When the reaction temperature was raised to 150° C., and the contact time reduced to 39 seconds, conversion increased to 86% and selectivity remained at 100%. (Table 1, Ex. 6b.)

II. Fluorination using a $Cr/Ni/AlF_3$ catalyst

EXAMPLE 7:

The preparation and activation of the catalyst ($Cr/Ni/AlF_3$) were performed substantially as described in Example 1A of European Patent Publication No. 0 486 333 A1.

In a rotary evaporator was placed 250 ml of a support containing, by weight, 73% aluminum fluoride and 27% alumina (obtained by hydrofluorination of Grace HSA Alumina in a fluidized bed reactor at 300° C. with a mixture of air and hydrofluoric acid), containing 5 to 10 volume % of hydrofluoric acid. Then, two separate aqueous solutions were prepared:

a) A chromic (acid) solution with nickel chloride added, containing:
    Anhydrous chromic (acid): 12.5 g
    nickel chloride hexahydrate: 29 g
    water: 40 g and b) A methanol solution containing:
    methanol: 17.8 g
    water: 50 g A mixture of these two solutions was then introduced at ambient temperature and under atmospheric pressure over about 45 minutes into the support under agitation. The catalyst was then dried under a flow of nitrogen on a fluid bed at around 100° C. for 4 hours.

The catalyst (63.1 grams) was placed into the reactor. The catalyst was dried at 300° C. using 20 cc/m of nitrogen for five hours, followed by HF gas activation (15 cc/m, which was gradually increased to 40 cc/m over 4 hours). The process of HF activation was maintained for 18 hours. Subsequently, a mixture of HF (60 cc/m) and 142b (20 cc/m) were fed over the catalyst bed at 140° C. The contact time was 47 seconds. Conversion was 100% and selectivity was also 100%. The process ran continuously for 170 hours without any evidence of catalyst deactivation or deterioration. This is a clear indication that Cr/Ni/AlF$_3$ is an excellent catalyst to hydrofluorinate 142b to 143a.

EXAMPLE 8:

After activating the catalyst as described in Example 7, a mixture of HF and 142b in a molar ratio of 1.3:1 was fed to the reactor at such rate as to provide a contact time of 11.4 seconds. The reaction temperature was 70° C. Conversion was 2.2% and selectivity for 143a was 100%. (Table 2, Run 1) When the process ran at 100° C., conversion was 99.5% and selectivity was 100%. (Table 2, Run 2) The process ran under these conditions for 40 hours. Upon lowering the temperature to 70° C., conversion was reduced to 88.9% and 143a selectivity remained at 100%. (Table 2, Run 3) This shows that the Cr/Ni/AlF$_3$ catalyst can be further activated during the process of feeding 142b and HF.

EXAMPLE 9: Effect of high temperature on the performance of the Cr/Ni/AlF$_3$ catalyst.

When the same mixture was fed to the same catalyst as in Example 8 at 300° C., with a contact time of 6.9 seconds, conversion was still very high (99.8%); however, selectivity for 143a was reduced to 99.4%. Other products were: VF$_2$ (selectivity=0.17%), VClF (0.12%) and VDC (0.27%). (Table 2, Run 4) Upon increasing the temperature further to 320° C., with a contact time of 6.6 seconds, conversion remained at 99.8%, but selectivity for 143a was further lowered to 98.2%; 1132a product increased to 0.56%, VClF to 0.37%, and VDC to 0.85%. (Table 2, Run 5) When the temperature was decreased to 275° C., conversion was 99.9% and selectivity for 143a was 99.7%; 1132a was now reduced to 0.07%; 1131a to 0.04%; and 1130a to 0.13%.

(Table 2, Run 6) We believe that the co-products were formed as a result of two consecutive disproportionation processes followed by HCl elimination from 140a as shown below:

1) 142b—>143a+141b
2) 141b—>142b+140a
3) 140a—>VDC+HCl

A summary of the results of Examples 8 and 9 is shown in Table 2. The data in Table 2 indicate that, to avoid olefin formation, process temperature should not exceed 275° C. at a molar ratio of HF/142b below 1.3:1.

EXAMPLE 10: Effect of 141b on the performance of the Cr/Ni/AlF3 catalyst.

The same catalyst used in Example 9 was used to evaluate the effect of 141b in the feed stream. When the following composition: 142b (16.49%), 141b (17.72%), HF (65.78%), molar ratio of HF:2×141b+142b=1.92, was fed at 100° C., at a contact time of 11.5 seconds, over the catalyst bed, conversion was very high (99.6%) and selectivity for 143a was also very high (99.9%). There was no evidence of olefin formation or other co-products. This means that a Cr/Ni/Fluorided Alumina catalyst can be used to hydrofluorinate both 141b and 142b without making undesirable by-products.

EXAMPLE 11: Effect of co-feeding 141b and HCl on the performance of Cr/Ni/Fluorided Alumina at various temperatures.

The following molar composition: 11% 142b, 12% 141b, 32% HCl and 45% HF, molar ratio of HF:2×141b+142b=1.92, was fed at various temperatures (100°–240° C.) and contact times. Conversion was generally >99.0% and selectivity for 143a was 100%, as shown in Table 3. These results suggest that it is possible to feed an impure stream of 142b, containing HCl and 141b, without making co-products.

EXAMPLE 12: Fluorination of 142b in the absence of catalysts. (Comparative Example)

When a mixture of HF and 142b was fed to the reactor at a temperature of 140° C., with a molar ratio of 3:1 of HF:142b, and a contact time 47 seconds, in the absence of catalyst, conversion was zero %. This indicates that the hydrofluorination of 142b to 143a requires a catalyst.

EXAMPLE 13: Evaluation and regeneration of the spent Cr/Ni/Fluorided Alumina catalyst.

Spent catalyst from the pilot plant (which was evaluated under conditions to produce high levels of olefin) containing 12% by weight of carbonaceous material was evaluated using processing conditions which are known to produce very high conversion and high selectivity to 143a as shown below (entry 1).

| Catalyst | T °C. | m.r. HF/142b | Contact Time Seconds | % Conversion | % Selectivity (143a) |
|---|---|---|---|---|---|
| 1) spent | 100 | 1.34 | 11.9 | 2.96 | 78.7 |
| 2) regenerated | 100 | 1.34 | 11.9 | 99.53 | 99.98 |

The spent catalyst was regenerated by heating the catalyst (20 g) at 350° C. using 20 cc/m of air for 40 hours, followed by 40 cc/m for 16 hours also at 350° C. and finally at 400° C. for 24 hours using 40 cc/m air. The catalyst was then evaluated under similar conditions (entry 2). Conversion was 99.53% and selectivity for 143a was 99.98%. This indicates that the cause of catalyst deactivation is carbonaceous deposit, and the best method to regenerate the catalyst is by using hot air.

TABLE 1

Summary of the pelletized CrF₃ catalyst performance.

| Ex. | T °C. | 142b × 10³ | 141b × 10³ | HCl × 10³ | HF/ (2 × 141b + 142b) | Cont. Time Sec. | Cat. age. hours | % Conv. | % Selectivity |
|---|---|---|---|---|---|---|---|---|---|
| 1 | 200 | 1.4 | 0 | 0 | 1.47 | 35.6 | 32 | 100 | 100 |
| 2 | 200 | .49 | .49 | 0 | 1.33 | 39.7 | 56.2 | 100 | 100 |
| 3 | 200 | .49 | .49 | 1.5 | 1.33 | 24.4 | 121.9 | 99.9 | 99.9 |
| 4 | 250 | .49 | .49 | 1.5 | 1.33 | 23.8 | 149.9 | 99.9 | 99.9 |
| 5a | 250 | .98 | .98 | 1.5 | 1.33 | 17.8 | 223.7 | 99.9 | 99.9 |
| 5b | 250 | .98 | .98 | 1.5 | 1.33 | 12.9 | 247.1 | 99.9 | 99.9 |
| 5c | 300 | .98 | .98 | 1.5 | 1.33 | 11.7 | 431.1 | 99.5 | 99.1 |
| 6a | 100 | .98 | 0 | 0 | 1.33 | 44.9 | 63 | 17 | 100 |
| 6b | 150 | .98 | 0 | 0 | 1.33 | 39 | — | 86 | 100 |

TABLE 2

Effect of reaction temperature on the product distribution for Cr/Ni/AlF₃.

| | Process Conditions | | | % Selectivity | | | |
|---|---|---|---|---|---|---|---|
| Run | Temp. °C. | m.r HF/ 142b | Contact Time Seconds | % Conversion | 143a | VF₂ | 141b | VDC |
| 1 | 70 | 1.3 | 11.4 | 2.2 | 100 | | | |
| 2 | 100 | 1.3 | 10.6 | 99.5 | 100 | | | |
| 3 | 70 | 1.3 | 11.3 | 88.9 | 100 | | | |
| 4 | 300 | 1.3 | 6.9 | 99.8 | 99.4 | .17 | .12 | .27 |
| 5 | 320 | 1.3 | 6.6 | 99.8 | 98.2 | .56 | .37 | .85 |
| 6 | 275 | 1.3 | 7.2 | 99.9 | 99.7 | .07 | .04 | .13 |

TABLE 3

Example 11, Summary of Results
Catalyst: Cr/Ni/Fluorided Alumina
FEED: 11% 142b, 12% 141b, 32% HCl, 45% HF

| Temperature (°C.) | Contact Time (Sec.) | Conversion (%) | Selectivity (143a, %) |
|---|---|---|---|
| 100* | 11 | 99.7 | 100 |
| 100 | 8 | 97.8 | 100 |
| 140 | 7 | 99.9 | 100 |
| 190 | 6 | 99.97 | 100 |
| 240 | 6 | 99.96 | 100 |

*No HCL in feed

EXAMPLE 14: Use of Cr/Ni/AlF₃ catalyst at high pressure.

A new feed system was added to the test reactor to allow operation at higher pressures. A 12 inches×¾ inch I.D. Hastelloy C reactor in a three zone electric furnace, identical to the reactor used in Examples 1–13, was used. The product gas also passed through a recirculating KOH scrubber and Drierite bed to an automatic on-line sample valve, and into an HP 5890 gas chromatograph equipped with a capillary column and FID. This system differed from that of the previous examples in that a back pressure regulator was provided between the reactor and the scrubber and two liquid feed pumps. These were Milton Roy model A771-257 pumps with Teflon diaphragms and a capacity of 26 ml/min. The pumpheads were cooled to about −5° C. The HF pressure was increased to about 40 psig with Helium. The two feed streams were vaporized separately in Hastelloy tubes wrapped with heat tape.

The Cr/Ni/AlF₃ catalyst was loaded and activated as described in Example 7 above. HF and 142b were fed at a molar ratio of 3.2:1 for a 7 second contact time at 100 psig. The temperature profile was controlled to simulate an adiabatic reactor with an inlet temperature of 120° C. and an outlet temperature of 325° C. Conversion was 100%, and selectivity to 143a was 100%.

Next, the 142b feed rate was increased, and the HF feed rate was decreased to change the HF:142b molar ratio to 2.5:1, while maintaining all the other conditions the same. Conversion and selectivity were still both 100%. Finally, the HF:142b ratio was reduced to 2:1. Unsaturated coproduct (mainly VDC) levels varied between about 0.01% and 1%. These results are summarized in Table 4. A comparison of these results with those of Example 9 shows that olefin production occurs at high temperature and low HF:142b ratios.

TABLE 4

Effect of HF: 142b molar ratio on product distribution using: Cr/Ni/AlF₃, 325° C., 100 psig, contact time = 7 seconds

| HF/142b (m.r.) | Conversion (%) | Selectivity to 143a (%) | Selectivity to VDC (%) |
|---|---|---|---|
| 3.2 | 100 | 100 | 0 |
| 2.5 | 100 | 100 | 0 |
| 2.0 | 100 | 99.0–99.99 | 0.01–1 |

Process For Removal of Low Level of Olefinic Material From 143a

The maximum allowable level of olefinic compounds in 143a (particularly if for use in a blend with 125 and 134a as a 502 refrigerant substitute) is 10 ppm. The olefinic compounds have been identified as 1,1-dichloroethylene (1130a), 1,1-difluoroethylene (1132a) and 1-chloro-1-fluoroethylene (1131a). As seen from Example 14, above, these olefinic materials can appear as a co-products in the 143a synthesis, depending on the operating conditions. For example, if the reactor temperature exceeds 275° C. and the molar ratio of HF/142b is less that 2:1, a high level (approximately 1%) of these compounds can be formed.

Therefore, we have investigated the feasibility of efficiently hydrofluorinating these compounds to the corresponding saturated products 141b, 142b and 143a, as shown below:

-continued

This process can be carried out in a separate fixed bed post-reactor, downstream from the main reactor, without distilling HCl or HF from the crude product. The post reactor contains the same catalyst, Cr/Ni/AlF$_3$, as the main reactor. However, the temperature used for operating this downstream reactor is much lower than the main reactor temperature. In general, the operable temperature range is from about 25° C. to about 200° C. In practice, it is preferable to operate at a temperature between about 50° C. and 100° C.

EXAMPLE 15: Removal of low level of 1132a and 1130a in 143a in absence of HCl

The catalyst, Cr/Ni/AlF$_3$ (38.8 grams), was charged to the 12 inch×¾ inch reactor. The catalyst was activated first at 100° C. using 25 cc/m of nitrogen for two hours, followed by feeding a blend of HF (25 cc/m) and nitrogen (25 cc/m) at 200° C. for 18 hours. Subsequently, the following composition (in moles): 143a (90.91%), 1130a (4.545%), 1132a (4.545%), using a 1:1 molar ratio of HF to 143a, was fed at 70° C., with a contact time of 11 seconds. After running for 86 hours, gas chromatography (gc) analysis showed the following composition: 143a (99.917%), 141b (0.045%) and 142b (0.038%), indicating 100% conversion of olefin present in the feed to the saturated compounds 141b and 142b. (Example 15, Table 5.)

EXAMPLE 16: Removal of low level of olefins 1132a and 1130a from 143a by hydrofluorination in the presence of HCl.

The above experiment was repeated in the presence of HCl, the molar ratio of HCl/HF/143a being 2:1:1, and the organic feed composition in moles being 143a (90.910%), 1130a (4.545%) and 1132a (4.545%), at 70° C., contact time 5.6 seconds. After running for 33 hours, gas chromatography analysis of the organic stream showed 143a (99.688%), 1130a (~0.001%), 141b (0.023%) and 142b (0.288%). A summary of the data is shown in Table 5.

EXAMPLES 17 and 18: Effect of contact time on the hydrofluorination of 1130a, 1132a in the presence of HCl.

EXAMPLE 17:

The process of Example 16 was repeated at 100° C., contact time 5.2 seconds. GC analysis of the organic stream showed 99.95% of 143a and 0.05% of 142b, indicating complete conversion of olefins to saturated product. (Example 17, Table 5.)

EXAMPLE 18:

Repeating Example 17, but reducing the contact time to 4 seconds, and using the same feed composition at 100° C., gave the following results by gas chromatograph analysis, after running for 360 hours: 143a (99.577%), 1130a (0.001%), 141b (0.009%) and 142b (0.413%), as shown in Table 5.

EXAMPLE 19: Removal of low level of 1130a, 1131a and 1132a from 143a in the presence of HCl A mixture of 143a (86.956%), 1130 (4.348%), 1132a (4.348%), 1131a (4.348%) was hydrofluorinated using a 1:1:1 molar ratio of HF/143a/HCl, at 100° C., 4 seconds contact time, using the same batch of catalyst as in Example 18. GC analysis of the product obtained after running for 48 hours showed 99.896% of 143a, 0.011% of 141b and 0.093% of 142b. There was no evidence of the presence of olefinic material, indicating 100% conversion of olefins (Example 19, Table 5).

EXAMPLE 20: Effect of co-feeding 141b and 365 at high pressure

The Cr/Ni/AlF3 catalyst was prepared and activated as described in Example 7 in the reactor described in Example 14. The reactor was maintained at 300° C. and 125 psig. A mixture of 90 mole % 142b and 10 mole % 141b was fed with HF at a molar ratio of HF/(142b+2×141b) of 5:1 at a contact time of 13 seconds. Conversion was 100% and selectivity for 143a was 100%.

Next, the organic feed was replaced by a feed comprising 83.1 mole % 142b, 9.4 mole % 141b and 7.5 mole % 365 (1,1,1,3,3-pentafluorobutane). The molar ratio of HF/(142b+2×141b) was maintained at 5:1. The 142b and 141b were again completely converted to 143a. The 365 was unreacted and did not affect the catalyst performance.

TABLE 5

Summary of Olefins Removal

| | | Inlet Feed Composition Mole % | | | | | Process Conditions | | Products Wt. % | | | | | |
| --- | --- | --- | --- | --- | --- | --- | --- | --- | --- | --- | --- | --- | --- | --- |
| | | | | | | | T °C. | Con. Time Sec. | 143a | VCl$_2$ | VF$_2$ | 141b | 142b | VClF |
| | VClF | 143a | VCl$_2$ | VF$_2$ | HF | HCl | | | | | | | | |
| Ex. 15 | a) 0 | 47.619 | 2.381 | 2.381 | 47.619 | 0 | 70 | 11 | 99.917 | 0 | 0 | .045 | .038 | 0 |
| | b) 0 | 90.91 | 4.546 | 4.546 | | | | | | | | | | |
| Ex. 16 | 0 | 24.391 | 1.219 | 1.219 | 24.391 | 48.780 | 70 | 5.6 | 99.688 | <.001$^{(1)}$ | 0 | .023 | .288 | 0 |
| | 0 | 90.910 | 4.545 | 4.545 | | | | | | | | | | |
| Ex. 17 | 0 | 24.391 | 1.219 | 1.219 | 24.391 | 48.780 | 100 | 5.2 | 99.95 | 0 | 0 | 0 | .05 | 0 |
| | 0 | 90.910 | 4.545 | 4.545 | | | | | | | | | | |
| Ex. 18 | 0 | 24.391 | 1.219 | 1.219 | 24.391 | 48.780 | 100 | 4.0$^{(2)}$ | 99.577 | .001 | 0 | .009 | .413 | 0 |
| | 0 | 90.910 | 4.545 | 4.545 | | | | | | | | | | |

TABLE 5-continued

Summary of Olefins Removal

| | Inlet Feed Composition Mole % | | | | | | Process Conditions | | Products Wt. % | | | | | |
|---|---|---|---|---|---|---|---|---|---|---|---|---|---|---|
| | VClF | 143a | VCl$_2$ | VF$_2$ | HF | HCl | T °C. | Con. Time Sec. | 143a | VCl$_2$ | VF$_2$ | 141b | 142b | VClF |
| Ex. 19 | 1.587 | 31.746 | 1.587 | 1.587 | 31.746 | 31.746 | 100 | 4$^{(3)}$ | 99.896 | 0 | 0 | .011 | .083 | 0 |
| | 4.348 | 86.956 | 4.348 | 4.348 | | | | | | | | | | |

$^{(1)}$The highest we have seen and some times not present.
$^{(2)}$by adding nitrogen from the top.
$^{(3)}$By adding nitrogen from the top.
a) mole % in the total feed
b) mole % in the organic feed

EXAMPLES 21–26: Adiabatic Hydrofluorination

A diagram of a small pilot version of adiabatic apparatus used in Examples 21–26 is shown in FIG. 2. As shown, the reactor 312 comprises a 2 inch diameter Schedule 10 Hastelloy pipe 300, which, in the pilot model, is 8 ft in total length. A top flange 301 and a bottom flange 302 cover the top and bottom, respectively, of pipe 300. The bottom of catalyst bed 303 is about 6 inches above bottom flange 302. Between flange 302 and the bottom of bed 303 are spacers 304 and a few inches of activated carbon. The bottom of bed 303 is designed to be at the same axial location as the bottom temperature probe 305. The nine internal temperature probes are side entering RTD probes. This avoids the use of a conductive thermowell. In the illustrated embodiment, the RTD probes are spaced six inches apart for a total of four feet up the reactor 312.

The reactor 312 is completely enclosed with 1 inch of insulation 308. Outside this insulation, copper coil 309 is wound uniformly along the axial length of the reactor 312. Another 1 inch of insulation 110 is wrapped around the outside of the coil. Either steam or hot oil can be fed to the coil 309 to supply external heat to minimize the driving force for heat transfer from the reactor 312. The insulation between the coil and the reactor is designed to minimize heat transfer in either direction.

On the upstream side of reactor 312 is a double pipe heat exchanger (not shown) which vaporizes the 142b/HF feed mix. On the downstream side of reactor 312 is an in-line filter 315 followed by a control valve 317 to control pressure and then line 319 to a scrubbing and drying system (not shown) to remove acids. After scrubbing and drying, the reactor effluent is sent to an on-line gas chromatography device (GC) (not shown) to analyze the product.

EXAMPLE 21:

The adiabatic reactor described above (FIG. 2) was packed with 5.5 lbs of Cr/Ni/AlF$_3$ catalyst which had been activated by the procedure described in Example 7 above. Feed rates were 6 lbs/hr of 142b and 4 lbs/hr of HF (HF/142b mol ratio=3.35) and the pressure was 150 psig. The effluent gas was analyzed as 99.972 wt % 143a, with the balance being 142b. There was virtually no olefin down to detectable limits (i.e. <5 ppm). The axial temperature profile is shown below (Table 6):

TABLE 6

Temperature Profile Along Axis of Adiabatic Reactor

| Axial Length ft | Temp °C. |
|---|---|
| 0.0 | 121 |
| 0.5 | 123 |
| 1.0 | 125 |
| 1.5 | 127 |
| 2.0 | 130 |
| 2.5 | 134 |
| 3.0 | 148 |
| 3.5 | 284 |
| 4.0 | 271 |

The drop in temperature between 3.5 and 4.0 ft is due to reactor heat losses. The above steady state profile does not reveal the actual maximum bed temperature since this is located between the two probes. To find this maximum temperature, the feed rates were lowered by 10% to shift the temperature profile up the bed. The probe temperature reading at 3 ft climbed from 148° C. to a maximum of 295° C. Therefore, the adiabatic temperature rise was 174° C.

EXAMPLE 22:

The reactor configuration was identical to that of Example 21. Feed rates were the same as in Example 21, but pressure was lowered to 100 psig. Conversion to 143a was 99.970%, with the remainder being 142b. No olefins were detected. The axial temperature profile is shown below (Table 7):

TABLE 7

Temperature Profile Along Axis of Adiabatic Reactor

| Reactor Length ft | Temp °C. |
|---|---|
| 0.0 | 115 |
| 0.5 | 117 |
| 1.0 | 119 |
| 1.5 | 124 |
| 2.0 | 129 |
| 2.5 | 164 |
| 3.0 | 290 |

TABLE 7-continued

Temperature Profile Along Axis of
Adiabatic Reactor

| Reactor Length ft | Temp °C. |
|---|---|
| 3.5 | 280 |
| 4.0 | 272 |

When the feed rates were lowered by 10% as in Example 21, the maximum bed temperature was found to be 305° C. The adiabatic temperature rise was about 17° C. higher than in Example 21.

EXAMPLE 23:

The reactor configuration was the same as in Example 21. The feed rates were 7.0 lbs/hr of 142b and 3.5 lbs/hr of HF. This was an HF/142b molar feed ratio of 2.51. The reactor pressure was 150 psig. The conversion was 99.95%, with the balance being 142b. No olefins were detected (i.e. <5 ppm). The axial temperature profile is shown below (Table 8):

TABLE 8

Temperature Profile Along Axis of
Adiabatic Reactor

| Reactor Length ft | Temp °C. |
|---|---|
| 0.0 | 116 |
| 0.5 | 117 |
| 1.0 | 119 |
| 1.5 | 121 |
| 2.0 | 131 |
| 2.5 | 292 |
| 3.0 | 283 |
| 3.5 | 279 |
| 4.0 | 274 |

When the feed rates were lowered by 10% as in Example 21, the temperature climbed to 303° C. at 2.0 ft, indicating this to be the maximum bed temperature. The adiabatic temperature rise was 187° C.

EXAMPLE 24:

The reactor configuration was the same as in Example 21. The feed rates were 5.0 lbs/hr 142b and 4.0 lbs/hr HF. The pressure was 150 psig. The conversion was 99.98%, with the balance being 142b. There were no olefins detected (i.e. <5 ppm). The axial temperature profile is shown below (Table 9).

TABLE 9

Temperature Profile Along Axis of
Adiabatic Reactor

| Reactor Length ft | Temp °C. |
|---|---|
| 0.0 | 120 |
| 0.5 | 121 |
| 1.0 | 122 |
| 1.5 | 123 |

TABLE 9-continued

Temperature Profile Along Axis of
Adiabatic Reactor

| Reactor Length ft | Temp °C. |
|---|---|
| 2.0 | 126 |
| 2.5 | 145 |
| 3.0 | 250 |
| 3.5 | 242 |

When feed rates were lowered by 10%, the maximum bed temperature was found to be 262° C.

EXAMPLE 25:

The reactor configuration was the same as in Example 21. The 142b flow rate was 7.5 lbs/hr and the HF flow rate was 1.8 lbs/hr, for an HF/142b molar feed ratio of 1.8. The wt % 143a in the reactor effluent was 98.8%. The effluent also included 0.43% 142b, 690 ppm of 141b, and 230 ppm of 140a. The distribution of olefins in the reactor effluent was as follows: 5858 ppm of 1130a, 335 ppm of 1131a, and 87 ppm of 1132a. The axial temperature profile is shown below (Table 10):

TABLE 10

Temperature Profile Along Axis of
Adiabatic Reactor

| Reactor Length ft | Temp °C. |
|---|---|
| 0.0 | 108 |
| 0.5 | 110 |
| 1.0 | 114 |
| 1.5 | 119 |
| 2.0 | 154 |
| 2.5 | 336 |
| 3.0 | 324 |
| 3.5 | 316 |
| 4.0 | 306 |

When flow rates were lowered by 10%, the maximum bed temperature was identified as 356° C.

EXAMPLE 26:

The reactor configuration was the same as in Example 21. This experiment was designed to test the feasibility of using 141b and 142b as co-feeds. The 142b feed rate was 3 lbs/hr and the 141b feed rate also was 3 lbs/hr. The HF feed rate was 3.2 lbs/hr. The molar ratio of HF in excess of its stoichiometric requirement was 1.97. Conversion of both feeds was 99.97%. 1130a was a non-selective coproduct at a level of 190 ppm. The axial temperature profile is shown below (Table 11):

TABLE 11

| Temperature Profile Along Axis of Adiabatic Reactor | |
|---|---|
| Reactor Length ft | Temp °C. |
| 0.0 | 108 |
| 0.5 | 115 |
| 1.0 | 304 |
| 1.5 | 290 |
| 2.0 | 283 |
| 2.5 | 275 |
| 3.0 | 271 |
| 3.5 | 267 |
| 4.0 | 262 |

While the invention has been described herein with reference to specific embodiments, it is not limited thereto. Rather it should be recognized that this invention may be practiced as outline above within the spirit and scope of the appended claims, with such variants and modifications as may be made by those skilled in this art.

We claim:

1. A process for manufacturing 1,1,1-trifluoroethane (143a), which comprises contacting 1,1-difluoro-1-chloroethane (142b) with HF in the gas phase on the sole fluorinating agent, at a molar ratio of HF:1,1-difluoro-1-chloroethane of greater than 1, in the presence of a chromium salt catalyst and in the presence or absence of a co-feed selected from the group consisting of 1,1-dichloro-1-fluoroethane (141b), 1,1,1,3,3-pentafluorobutane (365) and HCl.

2. The process of claim 1, wherein the catalyst is unsupported.

3. The process of claim 1, wherein the catalyst is supported.

4. The process of claim 1, wherein said chromium catalyst is prepared by activating a chromium salt selected from the halides, oxides, oxyhalides, nitrates and sulfates of chromium.

5. The process of claim 4, wherein the selected salt is $CrF_3 \cdot 4H_2O$.

6. The process of claim 1 which is performed without co-feeding air or other oxygen containing gas.

7. The process of claim 3, which results in the formation of less than 10 ppm of olefin byproduct.

8. The process of claim 1, wherein the reaction is conducted at a temperature between 30° C. and 400° C.

9. The process of claim 8, wherein the reaction temperature is between 30° C. and 280° C.

10. The process of claim 8, wherein the reaction temperature is between 280° C. and 350° C.

11. The process of claim 1, wherein the molar ratio of HF to 1,1-difluoro-1-chloroethane is from greater than 1:1 to 20:1.

12. The process of claim 11, wherein said molar ratio is from greater than 1:1 to 10:1.

13. The process of claim 11, wherein said molar ratio is from greater than 2.5:1 to 10:1.

14. The process of claim 11, wherein said molar ratio is from greater than 2.5:1 to 5:1.

15. The process of claim 10, wherein the molar ratio of HF to 1,1-difluoro-1-dichloroethane is at least about 2.5:1.

16. The process of claim 1, wherein the reaction is conducted at a pressure between atmospheric and 200 psig.

17. The process of claim 1, wherein the reaction is conducted at a pressure between atmospheric and 150 psig.

18. The process of claim 1, wherein the contact time is from 1 to 100 seconds.

19. The process of claim 1, wherein said contacting is performed in the presence of a cocatalyst for said chromium salt, said cocatalyst being selected from nickel, cobalt, manganese and zinc salts.

20. The process of claim 19, wherein said cocatalyst is selected from Ni, and Co salts.

21. The process of claim 20, wherein said cocatalyst is selected from Ni salts.

22. The process of claim 3, wherein the catalyst support is selected from activated carbon, alumina and fluorided alumina.

23. The process of claim 22, wherein said support is fluorided alumina.

24. The process of claim 23, wherein said catalyst is $Cr/Ni/AlF_3$.

25. The process of claim 1, which is performed in the presence of an impurity selected from 1,1-dichloro-1-fluoroethane, 1,1,1,3,3-pentafluorobutane and HCl.

26. The process of claim 1 which is performed under substantially isothermal conditions.

27. The process of claim 1 which is performed under substantially adiabatic conditions.

28. The process of claim 1 which comprises the further steps of passing the reaction product to a second reactor and contacting said reaction product in the vapor phase with HF in the presence of said catalyst, whereby any residual olefin impurities are hydrofluorinated.

29. The process of claim 28, wherein the temperature in said second reactor is from 30° C. to 150° C.

30. The process of claim 28, wherein the reaction product from the second reactor is fractionated.

* * * * *

UNITED STATES PATENT AND TRADEMARK OFFICE
CERTIFICATE OF CORRECTION

PATENT NO. : 5,639,924
DATED : June 17, 1997
INVENTOR(S) : Elsheikh, et. al.

It is certified that error appears in the above-indentified patent and that said Letters Patent is hereby corrected as shown below:

Column 19, claim 1, line 27, delete the word "on" and substitute therefor -- as --.

Signed and Sealed this

Twenty-third Day of September, 1997

Attest:

BRUCE LEHMAN

Attesting Officer

Commissioner of Patents and Trademarks